(12) United States Patent
Gauthier et al.

(10) Patent No.: US 11,020,407 B2
(45) Date of Patent: Jun. 1, 2021

(54) CORTICOSTEROID CONTAINING FOAM COMPOSITIONS AND METHOD OF MANUFACTURE THEREOF

(71) Applicant: MAYNE PHARMA LLC, Greenville, NC (US)

(72) Inventors: Robert T. Gauthier, San Diego, CA (US); James D. Hammer, Uxbridge, MA (US)

(73) Assignee: MAYNE PHARMA LLC, Greenville, NC (US)

( * ) Notice: Subject to any disclaimer, the term of this patent is extended or adjusted under 35 U.S.C. 154(b) by 0 days.

(21) Appl. No.: 15/365,152

(22) Filed: Nov. 30, 2016

(65) Prior Publication Data

US 2017/0165276 A1    Jun. 15, 2017

Related U.S. Application Data

(60) Provisional application No. 62/267,773, filed on Dec. 15, 2015.

(51) Int. Cl.

| | | |
|---|---|---|
| *A61K 9/12* | (2006.01) | |
| *A61K 31/573* | (2006.01) | |
| *A61K 9/00* | (2006.01) | |
| *A61K 31/58* | (2006.01) | |
| *A61K 47/06* | (2006.01) | |
| *A61K 47/10* | (2017.01) | |
| *A61K 47/12* | (2006.01) | |
| *A61K 47/44* | (2017.01) | |
| *B65B 31/00* | (2006.01) | |
| *B65B 63/08* | (2006.01) | |
| *B65D 83/14* | (2006.01) | |

(52) U.S. Cl.
CPC .......... *A61K 31/573* (2013.01); *A61K 9/0014* (2013.01); *A61K 9/122* (2013.01); *A61K 31/58* (2013.01); *A61K 47/06* (2013.01); *A61K 47/10* (2013.01); *A61K 47/12* (2013.01); *A61K 47/44* (2013.01); *B65B 31/003* (2013.01); *B65B 63/08* (2013.01); *B65D 83/752* (2013.01)

(58) Field of Classification Search
CPC .... A61K 9/0014; A61K 9/122; A61K 31/573; A61K 31/58; A61K 47/06; A61K 47/10; A61K 47/12; A61K 47/44; B65B 31/003; B65B 63/08; B65D 83/752
See application file for complete search history.

(56) References Cited

U.S. PATENT DOCUMENTS

| | | | | |
|---|---|---|---|---|
| 5,167,950 | A | * | 12/1992 | Lins ........................ A01N 25/16 424/47 |
| 6,126,920 | A | * | 10/2000 | Jones ................... A61K 9/0014 424/45 |
| 2005/0069499 | A1 | | 3/2005 | Arkin et al. |
| 2006/0018937 | A1 | | 1/2006 | Friedman et al. |
| 2006/0171898 | A1 | | 8/2006 | Jones |
| 2008/0015271 | A1 | | 1/2008 | Abram |
| 2013/0209545 | A1 | | 8/2013 | Twidwell |

FOREIGN PATENT DOCUMENTS

| | | |
|---|---|---|
| WO | WO 1996/027376 A1 | 9/1996 |
| WO | WO 2015/044857 A1 | 4/2015 |

OTHER PUBLICATIONS

Bernhard et al. J Am Acad Derm. 1991; 25(6): abstract. (Year: 1991).*
Cravotto et al. Steroids. 2007; 72: 787-791. (Year: 2007).*
International Search Report dated Feb. 28, 2017, regarding PCT/IB2016/057227.

* cited by examiner

*Primary Examiner* — David Browe
(74) *Attorney, Agent, or Firm* — Nath, Goldberg & Meyer; Joshua B. Goldberg; Scott H. Blackman (57) ABSTRACT

The present invention provides a method for treating various skin diseases by topically administering to a subject a composition formulated as a foamable composition which includes a corticosteroid, such as halobetasol. The composition may include a corticosteroid, ethyl alcohol, emulsifying wax, cetostearyl alcohol, polyoxyl 20 cetostearyl ether, water, benzoic acid and propellant.

11 Claims, 5 Drawing Sheets

ODS at Baseline and Days 8 and 15 (ITT Population)*

ITT = Intent to Treat (i.e., Includes all subjects to whom drug was dispensed.)
PP = Per Protocol (i.e., Subjects were treated in accordance with the study protocol.)

CORTICOSTEROID CONTAINING FOAM COMPOSITIONS AND METHOD OF MANUFACTURE THEREOF

RELATED APPLICATION DATA

This application claims the benefit of priority under 35 U.S.C. § 119(e) of U.S. Provisional Patent Application Ser. No. 62/267,773, filed Dec. 15, 2015, the entire contents of which is incorporated herein by reference in its entirety.

BACKGROUND

Field of Invention

This invention relates to foamable compositions including a corticosteroid, and more particularly to a method of manufacturing stable foamable compositions.

Background Information

Corticosteroids are well known anti-inflammatory compounds, which are recognizably utilized in the treatment of inflammatory diseases such as allergic contact dermatitis, eczema, asteatotic eczema, discoid eczema, infantile eczema and diaper dermatitis, psoriasis; including plaque psoriasis, palmoplantar psoriasis, etc., seborrheic dermatitis, atopic dermatitis, dermatitis herpetiformis, neurodermatitis, lichen simplex chronicus, lichen planus, subacute cutaneous lupus erythematosus, urticaria, discoid lupus erythematosus, chronic hypertrophic lichen planus, granuloma annulare, keloid scars, reactions to insect and spider bites, *Pityriasis rosea*, erythema, and pruritus. Formulations containing such active substances have conventionally been applied to the skin site in the form of foams, ointments, gels, creams, sprays and lotions.

Foamable compositions are particularly desirable for topical application of corticosteroids. However, a number of problems exist in conventional methods of manufacturing corticosteroid foams, such as degradation and inactivation of the corticosteroid during manufacture and canning of the foam composition. Additional problems include corticosteroid degradation over the shelf life of the composition.

As such, there exists a need in the treatment of skin disorders requiring treatment with corticosteroids for improved formulations manufactured by methods which prevent degradation and inactivation of the corticosteroid and which exhibit prolonged stability of the corticosteroid thereby exhibiting extended shelf life as compared to conventional foam compositions manufactured by conventional means.

SUMMARY

The manufacturing method and foamable compositions produced by such method as presented herein do not utilize a traditional buffer system which adds manufacturing complexity. However, compositions manufactured by the presently described method exhibit a stable pH, enhanced stability of corticosteroids, and enhanced efficacy in treatment as compared to other treatment options.

The compositions of the present invention demonstrate a clinical efficacy which is superior to comparable corticosteroid containing compositions. In addition, it has been found that the compositions of the present invention are stable and demonstrate very good long term storage stability.

As will be further explained herein below, compositions manufactured by the presently described method achieve a high level of clinical efficacy without appreciably reducing transepidermal water loss (TEWL). Skin conductance studies have also demonstrated that the compositions of the present invention do not appreciably increase skin hydration. The compositions of the present invention comprise particular combinations of ingredients which interact synergistically to produce the enhanced results described herein without increasing skin hydration or reducing transepidermal water loss.

Accordingly, in one aspect, the present invention provides a method for single-stream manufacture of a foamable composition including a corticosteroid. The method includes forming a homogenous solution which includes: i) an aliphatic alcohol; ii) a can corrosion inhibitor; iii) a polyol; iv) at least one foam structuring agent comprising one or more fatty alcohols, non-ionic surfactants, or combinations thereof; and v) water. In embodiments, the solution is formed in a single batch vessel at a constant temperature of between about 55°-75° C. while minimizing evaporative losses. Subsequently, the mixture is cooled to a temperature of between about 40°-55° C. and a corticosteroid is then added to the solution and mixed to homogeneity while maintaining a temperature of between about 40°-55° C. The solution is then filled into dispensing canisters while the solution is maintained at a temperature of between about 40°-50° C. The filled canisters are then charged with a propellant thereby forming a single-phase foamable composition.

In another aspect, the present invention provides a greater than 36-month storage stable, corticosteroid containing foamable composition produced by the method of manufacture described herein. The composition includes: a) a corticosteroid, or its pharmaceutically acceptable salts, esters, and solvates; b) an aliphatic alcohol; c) at least one foam structuring agent (including one or more fatty alcohols, one or more non-ionic surfactants, or combinations thereof); d) a polyol; e) water; f) a can corrosion inhibitor; and g) a propellant. In embodiments, the composition is void of a buffer.

In one embodiment, the present invention is a stable, therapeutically effective composition consisting essentially of: a) halobetasol or its pharmaceutically acceptable salts, esters, and solvates; b) an aliphatic alcohol; c) at least one foam structuring agent selected from one or more fatty alcohols, one or more non-ionic surfactants, or combinations thereof; d) a polyol; f) water; and g) optionally, if the composition is stored in a metal container or can, benzoic acid as a can corrosion inhibitor. The composition is devoid of a buffer. The composition may be devoid of a second therapeutic agent in addition to halobetasol.

In another embodiment, the present invention is a stable composition consisting of: a) halobetasol or its pharmaceutically acceptable salts, esters, and solvates; b) an aliphatic alcohol; c) at least one foam structuring agent selected from one or more fatty alcohols, one or more non-ionic surfactants, or combinations thereof; d) a polyol; f) water; and g) optionally, if the composition is stored in a metal container or can, benzoic acid as a can corrosion inhibitor. The composition is devoid of a buffer. The composition may be devoid of a second therapeutic agent in addition to halobetasol.

In another aspect, the present invention provides a method for treating a subject having, or at risk of having, a corticosteroid-responsive condition, such as a skin disease or disorder. The method includes topically administering to the subject in need thereof a foamable composition of the present invention, thereby treating the corticosteroid-responsive condition. In some embodiments, the condition is a skin disorder or disease, such as a corticosteroid-responsive dermatosis, including for example, atopic dermatitis, seborrheic dermatitis, contact dermatitis, psoriasis, atopic eczema, infantile eczema, discoid eczema, lichen simplex, lichen planus, skin inflammation, miliaria, *Pityriasis rosea*, erythema, and pruritus.

DETAILED DESCRIPTION

Before the present compositions and methods are further described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

Preparation and Canning

One aspect of the present invention is a process for manufacturing a foamable corticosteroid containing composition as described herein. Generally, the method includes forming a carrier solution by admixing an aliphatic alcohol, a can corrosion inhibitor, one or more foam structuring agents, such as a fatty alcohol and a non-ionic surfactant, a polyol, and water and heating to a temperature of at least 45° C., more preferably at least 65° C., while minimizing evaporative losses.

According to a feature of the present invention, a corticosteroid is added to the carrier at a temperature below 60° C., more preferably below 50° C. By adding corticosteroid at a lower temperature in the manufacturing process the rate of degradation of the corticosteroid is markedly reduced and thus the amount of degradant products is reduced.

According to yet another feature of the present invention the corticosteroid containing solution is filled into canisters at a temperature above 35° C., most preferably above 42° C. Filled canisters are then charged with a propellant to produce a clear single-phase foamable composition.

In particular, the method of the invention includes first forming a homogenous carrier solution which includes: i) an aliphatic alcohol; ii) a can corrosion inhibitor; iii) a polyol; iv) at least one foam structuring agent comprising one or more fatty alcohols, non-ionic surfactants, or combinations thereof; and v) water. In embodiments, the solution is formed in a single batch vessel at a constant temperature of between about 55°-75° C., and more preferably between about 65°-70° C., while minimizing evaporative losses.

In one embodiment, an aliphatic alcohol, such as ethanol, is first heated in a single batch vessel to between about 65°-70° C. and a can corrosion inhibitor, such as benzoic acid, is then added. The solution is mixed to homogeneity and subsequently the following components are admixed in series while maintaining a temperature of between about 65°-70° C.: a polyol (e.g., propylene glycol); and foam structuring agents (e.g., combinations of Emulsifying wax, polyoxyl 20 cetostearyl ether, and cetostearyl alcohol). Water is added in multiple aliquots to maintain a temperature greater than 55° C. and the completed carrier solution is heated to 65°-70° C. and mixed to homogeneity.

Subsequently, the solution is cooled to a temperature of between about 45°-50° C. and a corticosteroid is then added to the solution and mixed to uniformity while maintaining a temperature of between about 45°-50° C. Total evaporative losses are kept below 1.0% w/w, and more preferably below 0.25% w/w, during compounding through the use of a suitable manufacturing vessel with a pressure and/or vacuum rated lid that seals onto the vessel.

Throughout the admixing process, the bulk solution may be analyzed to ensure proper mixing and temperature of the solution. Once the corticosteroid is added, the solution is mixed to uniformity. The solution is then filled into aerosol canisters while the solution is maintained at a temperature of between about 42°-48° C. Preferably, the solution is mixed for at least 30 minutes or more before being filled into the dispensing canisters. The filled canisters are then charged with a propellant thereby forming a single-phase foamable composition.

According to one embodiment of the present invention the canisters are made of metal having an internal resistance burst pressure of at least 270 PSIG, more preferably tin or aluminum, and are lined to prevent degradation and corrosion. Another feature of the present invention is an aerosol valve, more preferably an inverted-dispensing valve. Yet another feature of the present invention is an actuator and valve combination capable of dispensing foam at a controlled rate with preferred cosmetic characteristics.

Compositions

The present invention provides a greater than 36-month storage stable, foamable composition produced by the method described herein for treating a corticosteroid-responsive condition, including skin diseases and disorders, such as corticosteroid-responsive dermatoses. The composition includes: a) a corticosteroid, or its pharmaceutically acceptable salts, esters, and solvates; b) an aliphatic alcohol;

c) one or more foam structuring agents (including one or more fatty alcohols, one or more non-ionic surfactants, or combinations thereof); d) a polyol; e) water; f) a can corrosion inhibitor; and g) a propellant. The composition is preferably void of a buffer. It should be understood that the stable, therapeutic composition can consist essentially of, or consist of, the above components.

The composition of the present invention is applied to the treatment site (after foaming) or a secondary site, such as a hand (after foaming), for application to the treatment site as a foam. Upon application, the composition is initially in the form of a mousse-like foam which is engineered to break down at skin temperature under low application shear allowing the halobetasol or other corticosteroid to saturate the treatment site. The presently described system provides enhanced penetration of the halobetasol or other corticosteroid through the epidermis. The composition exhibits ideal characteristics between traditional rigid (mousse-like) and thermolabile (quick-break) foams that is achieved without buffering. It has been found that improved stabilization of corticosteroid is achieved through addition of a small amount of the can corrosion inhibitor benzoic acid. It should be understood that reference to the "can" herein refers to the canister from which the composition is delivered.

The aliphatic alcohol may preferably be chosen from methyl, ethyl, isopropyl and butyl alcohols, and mixtures of two or more thereof. In one embodiment, the aliphatic alcohol is ethyl alcohol. In embodiments, the aliphatic alcohol, such as ethyl alcohol, is included in the composition at between about 40-70%, 45-65%, 50-60%, or 55-60% w/w; or in an amount of about 45%, 46%, 47%, 48%, 49%, 50%, 51%, 52%, 53%, 54%, 55%, 56%, 57%, 58%, 59%, 60%, 61%, 62%, 63%, 64% or 65% w/w.

The present composition further includes one or more foam structuring agents, such as one or more fatty alcohols. The one or more fatty alcohols included in the composition of the present invention have a linear or branched carbon backbone that has 6-22 carbon atoms. In embodiments of the invention, the one or more fatty alcohols have a linear or branched carbon backbone that has 10-18 carbon atoms. In various embodiments the fatty alcohol is selected from the group consisting of lauryl alcohol, myristyl alcohol, cetyl alcohol, lauryl alcohol, stearyl alcohol, octyldodecanol, and combinations thereof. Yet other fatty alcohols will be apparent to those of skill in the art. In an embodiment, mixtures of cetyl alcohol and a stearyl alcohol are preferred, for example cetostearyl alcohol.

In embodiments, the fatty alcohol, such as cetostearyl alcohol, is included in the composition at between about 0.05-1.0%, 0.06-0.95%, 0.07-0.9%, 0.08-0.75%, 0.09-0.7%, 0.1-0.65%, 0.15-0.6%, 0.2-0.5%, 0.2-0.4% or 0.2-0.3% w/w; or in an amount of about 0.15%, 0.16%, 0.17%, 0.18%, 0.19%, 0.2%, 0.21%, 0.22%, 0.23%, 0.24%, 0.25%, 0.26%, 0.27%, 0.28%, 0.29%, 0.3%, 0.31%, 0.32%, 0.33%, 0.34%, 0.35% or 0.36% w/w.

The present composition further includes one or more foam structuring agents, such as one or more non-ionic surfactants. Non-ionic surfactants that may be used in the composition of the present invention generally include ethoxylated alcohols. Non-ionic surfactants that may be used in the composition of the present invention include glyceryl stearate, PEG 100-stearate, polyoxyl-20-cetostearyl ether, glyceryl monooleate, glyceryl palmitostearate, polyoxyl-20-stearate, polyoxyl-40-stearate, polyoxyl-60-stearate, polyoxyl-80-stearate, polyoxyl-20-oleate, polyoxyl-40-oleate, polyoxyl-60-oleate, polyoxyl-80-oleate, polyoxyl-20-palmitate, polyoxyl-40-palmitate, polyoxyl-60-palmitate, polyoxyl-80-palmitate, polyoxyethylene (20) sorbitan monolaurate, polyoxyethylene (20) sorbitan monopalmitate, polyoxyethylene (20) sorbitan monostearate, polyoxyethylene (20) sorbitan monooleate, laureth-2, laureth-4, laureth-6, and laureth-8. Yet other non-ionic surfactants will be apparent to those of skill in the art. In a preferred embodiment, the non-ionic surfactant is polyoxyl-20-cetostearyl ether. In embodiments, the non-ionic surfactant, such as polyoxyl-20-cetostearyl ether, is included in the composition at between about 0.05-1.0%, 0.06-0.95%, 0.07-0.9%, 0.08-0.75%, 0.09-0.7%, 0.1-0.65%, 0.15-0.6%, 0.2-0.5%, 0.2-0.4% or 0.2-0.3% w/w; or in an amount of about 0.15%, 0.16%, 017%, 0.18%, 0.19%, 0.2%, 0.21%, 0.22%, 0.23%, 0.24%, 0.25%, 0.26%, 0.27%, 0.28%, 0.29%, 0.3%, 0.31%, 0.32%, 0.33%, 0.34%, 0.35% or 0.36% w/w.

The present composition further includes one or more foam structuring agents including combinations of one or more fatty alcohols and one or more non-ionic surfactants. The fatty alcohol component is selected from the group consisting of lauryl alcohol, myristyl alcohol, cetyl alcohol, lauryl alcohol, stearyl alcohol, octyldodecanol, and combinations thereof. The non-ionic component is selected from the group consisting of glyceryl stearate, PEG 100-stearate, polyoxyl-20-cetostearyl ether, glyceryl monooleate, glyceryl palmitostearate, polyoxyl-20-stearate, polyoxyl-40-stearate, polyoxyl-60-stearate, polyoxyl-80-stearate, polyoxyl-20-oleate, polyoxyl-40-oleate, polyoxyl-60-oleate, polyoxyl-80-oleate, polyoxyl-20-palmitate, polyoxyl-40-palmitate, polyoxyl-60-palmitate, polyoxyl-80-palmitate, polyoxyethylene (20) sorbitan monolaurate, polyoxyethylene (20) sorbitan monopalmitate, polyoxyethylene (20) sorbitan monostearate, polyoxyethylene (20) sorbitan monooleate, laureth-2, laureth-4, laureth-6, and laureth-8. Yet other fatty alcohols and other non-ionic surfactants will be apparent to those skilled in the art. In a preferred embodiment, the fatty alcohol and non-ionic surfactant combination includes cetyl alcohol, stearyl alcohol, and one or more of polyoxyethylene (20) sorbitan monolaurate, polyoxyethylene (20) sorbitan monopalmitate, polyoxyethylene (20) sorbitan monostearate, polyoxyethylene (20) sorbitan monooleate, for example, Emulsifying Wax, NF.

In embodiments, the foam structuring agent(s) is included in the composition at between about 0.1-4.0%, 0.1-3.5%, 0.1-3.0%, 0.1-2.5%, 0.1-2.0%, 0.5-2.0%, 1.0-2.0%, 1.5-2.0% or 1.6-1.9% w/w; or in an amount of about 1.05%, 1.1%, 1.15%, 1.2%, 1.25%, 1.3%, 1.35%, 1.4%, 1.45%, 1.5%, 1.55%, 1.6%, 1.65%, 1.7%, 1.75%, 1.8%, 1.85%, 1.9%, 1.95% or 2.0% w/w.

In embodiments, Emulsifying Wax, NF, is included in the composition at between about 0.1-4.0%, 0.1-3.5%, 0.1-3.0%, 0.1-2.5%, 0.1-2.0%, 0.5-2.0%, 1.0-2.0%, 1.0-1.5% or 1.0-1.1% w/w; or in an amount of about 0.75%, 0.8%, 0.85%, 0.9%, 0.95%, 1.0%, 1.05%, 1.1%, 1.15%, 1.2%, 1.25%, 1.3%, 1.35%, 1.4%, 1.45%, 1.5%, 1.55%, 1.6%, 1.65% or 1.70%, 1.75%, 1.8%, 1.85%, 1.9%, 1.95% or 2.0% w/w.

The polyol component of the composition may function as a solubility enhancer for the corticosteroid and may have traditional humectant properties. Such polyols may include materials such as glycerin, propylene glycol, butylene glycol, dipropylene glycol, pentylene glycol, hexylene glycol, polyethylene glycol, and the like; and these polyol materials may be used either singly or in combination in the preparations of the present invention. In a preferred embodiment, the polyol is propylene glycol. In embodiments, the polyol solubility enhancer is included in the composition at between about 1-10%, 2-8%, 3-7%, or 4-6% w/w; or in an amount of about 1.0%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5% or 10.0% w/w; or in an amount of about 4.0%, 4.1%, 4.2%, 4.3%, 4.4%, 4.5%, 4.6%, 4.7%, 4.8%, 4.9%, 5.0%, 5.1%, 5.2%, 5.25%, 5.3%, 5.4%, 5.5%, 5.6%, 5.7%, 5.9%, 6.0%, 6.1%, 6.2%, 6.3%, 6.4%, 6.5%, 6.6%, 6.7%, 6.8%, 6.9% or 7.0% w/w.

The composition of the present invention may be contained in and dispensed from a container capable of withstanding the pressure of the propellant gas and having an appropriate valve and actuator for dispensing the composition as a foam under pressure. If the container is made of a material such as aluminum or tin that is likely to suffer corrosion under the action of the composition, in the event the internal lining suffers a breach, the composition may include a single corrosion inhibitor as an additive. Suitable corrosion inhibitors include organic acids, such as but not limited to sorbic acid, benzoic acid, formic acid, acetic acid, propionic acid, butyric acid, valeric acid, caproic acid, oxalic acid, lactic acid, malic acid, citric acid and carbonic acid. In embodiments, the can corrosion inhibitor is included in the composition at less than about 0.0015%, 0.001%, 0.0009%, 0.0008%, 0.0007%, 0.0006%, 0.0005%, 0.0004%, 0.0003%, 0.0002% or 0.0001%, w/w.

The propellant used may be chosen from conventional aerosol propellants. Thus, one may select the propellant from propane, n-butane, isobutane, n-pentane, isopentane, dichloro difluoro methane, dichloro tetrafluoro ethane, octafluoro cyclobutane, 1,1,1,2-tetrafluoroethane, 1,1-difluoroethane, 1,2,3,3,3-heptafluoropropane and mixtures of two or more thereof. The propellant level should be adjusted to optimize the quality of the foam and to produce traditional rigid (mousse-like) and thermolabile (quick-break) characteristics. In embodiments, the propellant is included in the composition at between about 2.75-6.25%, 3-6%, or 3.25-5.75% w/w; or in an amount of about 2.75%, 3%, 3.25%, 3.5%, 3.75%, 4%, 4.25%, 4.5%, 4.75%, 5%, 5.25%, 5.5%, 5.75%, 6%, or 6.25% w/w.

The present composition further includes an aqueous component, such as water. In embodiments, water is included in the composition at between about 25-45%, 30-40% or 35-40% w/w; or in an amount of about 25%, 26%, 27%, 28%, 29%, 30%, 31%, 32%, 33%, 34%, 35%, 36%, 37%, 38%, 39%, 40%, 41%, 42%, 43%, 44% or 45% w/w.

In specific embodiments of the present invention, the foregoing ingredients are present in particular ratios. A number of formulations may be prepared in accord with the present invention shown in Tables I-VI below, which list compositional ranges for such formulations.

TABLE I

Formulation Component Ranges

| Component | % w/w |
| --- | --- |
| Aliphatic alcohol | 40-60 |
| Foam structuring agents (fatty alcohols, non-ionic surfactants, and combinations thereof) | 0.1-4.0 |
| Polyol solubility enhancer | 1-10 |
| Water | 30-40 |
| Corrosion inhibitor | less than 0.001 |

TABLE II

Formulation Component Ranges

| Component | % w/w |
| --- | --- |
| Aliphatic alcohol | 50-60 |
| Fatty alcohol and/or non-ionic surfactant | 0.1-1.0 |
| Emulsifying Wax, NF | 0.5-2.0 |
| Polyol solubility enhancer | 2-8 |
| Water | 35-40 |
| Corrosion inhibitor | less than 0.001 |

TABLE III

Formulation Component Ranges

| Component | % w/w |
| --- | --- |
| Aliphatic alcohol | 50-60 |
| Emulsifying Wax, NF | 0.5-2.0 |
| Fatty alcohol | 0.1-0.4 |
| Non-ionic surfactant | 0.1-0.4 |
| Polyol solubility enhancer | 2-8 |
| Water | 35-40 |
| Corrosion inhibitor | less than 0.001 |

TABLE IV

Formulation Component Ranges

| Component | % w/w |
| --- | --- |
| Aliphatic alcohol | 50-60 |
| Emulsifying Wax, NF | 0.1-1.1 |
| Fatty alcohol | 0.2-0.3 |
| Non-ionic surfactant | 0.2-0.3 |
| Polyol solubility enhancer | 2-8 |
| Water | 35-40 |
| Corrosion inhibitor | less than 0.001 |

TABLE V

Formulation Component Ranges

| Component | % w/w |
| --- | --- |
| Ethyl alcohol | 40-60 |
| Emulsifying Wax, NF | 0.1-5.0 |
| Cetostearyl alcohol | 0.05-1.0 |
| Polyoxyl 20 cetostearyl ether | 0.05-1.0 |
| Propylene glycol | 1-10 |
| Water | 30-40 |
| Benzoic acid | less than 0.001 |

TABLE VI

Corticosteroid Formulations

| Component | % w/w |
| --- | --- |
| Corticosteroid | 0.05 |
| Ethyl alcohol | 50-60 |
| Emulsifying Wax, NF | 1.0-1.1 |
| Cetostearyl alcohol | 0.2-0.3 |
| Polyoxyl 20 cetostearyl ether | 0.2-0.3 |
| Propylene glycol | 2-8 |
| Water | 35-40 |
| Benzoic acid | less than 0.001 |

Preparations based upon the ratios set forth in Tables I-VI, include, or will further include the corticosteroid material and a propellant, and may also include ancillary ingredients such as preservatives, fragrances, coloring agents, viscosity control agents and the like. The corticosteroid is preferably present in an amount of about 0.01-1.0% w/w more preferably about 0.05-0.2% w/w. In embodiments, corticosteroids for use in the present invention include, by way of illustration and in no way limiting, the following: methylprednisolone, hydrocortisone, prednisolone, clobetasone, hydrocortisone butyrate, flumetasone, fluocortin, fluperolone, fluorometholone, fluprednidene, desonide, triamcinolone, alclometasone, hydrocortisone buteprate, dexamethasone, clocortolone, betamethasone, fluclorolone, desoximetasone, fluocinolone acetonide, fluocortolone, diflucortolone, fludroxycortide, fluocinonide, budesonide, diflorasone, amcinonide, halometasone, mometasone furoate, methylprednisolone aceponate, beclometasone, hydrocortisone aceponate, fluticasone, prednicarbate, difluprednate, halobetasol, resocortol butyrate, clobetasol and halcinonide. In a preferred embodiment, the corticosteroid is halobetasol, such as halobetasol propionate.

Unlike typical foam formulations, the composition of the present invention does not include a buffer system. As such, the composition is void of a traditional buffer. During preparation the minute amount of the can corrosion inhibitor added serves to maintain the product at a pH in the general range of about 4.0-6.3 and preferably about 5.0-5.5 at the time of manufacture. In embodiments, the preferred can corrosion inhibitor is benzoic acid at less than about 0.0015%, 0.001% or 0.0005% w/w.

Upon dispensing from the can the composition of the present invention is found to produce a rigid, mousse-like foam that remains thermally stable on the surface of the skin until applied with light shear to the application site. The thermal stability of the foam at about 32-37° C. has been demonstrated for up to at least 600 seconds. The thermal stability of the foam at about 20-25° C. has been demonstrated for up to at least 1200 seconds. Unexpectedly, it remains rigid and mousse-like at skin temperature but the foam behaves like a traditional thermolabile (quick-break) foam during application of shear forces, allowing for ease of use and application at the treatment site.

The composition of the present invention is found to exhibit very good stability under storage conditions. As is known in the art, corticosteroids may degrade under storage conditions. For example, halobetasol propionate can degrade under storage conditions with some of the degradation products or impurities produced including: halobetasol $\Delta_{16}$ analog; and halobetasol spiro analog.

The amount of degradation products of halobetasol material, such as degradation products of halobetasol propionate, is directly related to the amount of degradation of the halobetasol material.

Compositions of the present invention are storage stable such that the amount of degradation products of a halobetasol material therein after storage for six months at 40° C. is less than 5% and at storage for 24 months at 25° C. is less than 2% of the total amount of the halobetasol material contained therein at the time of manufacture.

The storage stability of compositions of the present invention can be demonstrated by the pH stability of the formulation, assay of the amount of halobetasol material, such as halobetasol propionate, and/or by assay of the amount of one or more degradation products of the halobetasol material.

In one embodiment, the composition of the present invention exhibits an acceptable shelf-life of greater than about 36, 39, 42, 45, 48 or more months. For example, in embodiments, the shelf-life of the present invention can be projected at greater than 36 months using standard analysis techniques, such as those described in the International Conference on Harmonisation of Technical Requirements for Registration of Pharmaceuticals for Human Use (ICH) Q1A (R2) guidance for industry, Stability Testing of New Drug Substances and Products (available on the World Wide Web at fda.gov/downloads/drugs/guidancecomplianceregulatoryinformation/guidances/ucm073369.pdf; and incorporated by reference herein in its entirety in particular for its teaching of analysis techniques that should be used). According to the guidance it is normally unnecessary to perform a formal statistical analysis on data that show little degradation and little variability. The recommended approach for analyzing data expected to change with time is to apply the 95 percent, one-sided confidence limit to the mean and to determine the time at which the confidence interval intersects the acceptance criterion.

In various embodiments, the composition of the present invention is stable, having an acceptable shelf-life of at least six months. In some embodiments the composition has an acceptable shelf-life of at least one year. In some embodiments the composition has an acceptable shelf-life of at least 15, 18, 21, 24, 27, 30, 33, 36, 39, 42, 45, 48 or more months at ambient temperature as determined by the analysis method described above (and used in Example 4 herein) in the International Conference on Harmonisation of Technical Requirements for Registration of Pharmaceuticals for Human Use (ICH) Q1A (R2) guidance for industry, Stability Testing of New Drug Substances and Products.

In some embodiments, compositions of the present invention are storage stable such that the amount of degradation products of a halobetasol material therein after storage for at least 15, 18, 21, 24, 27, 30, 33, 36, 39, 42, 45 or 48 months at 40° C. is less than about 10%, 9%, 8%, 7%, 6%, 5%, 4%, 3%, 2% or 1% of the total amount of the halobetasol material contained therein at the time of manufacture.

Methods of Treatment

In another aspect, the present invention provides a method for treating a subject having, or at risk of having, a corticosteroid-responsive condition, such as a skin disease or disorder. The method includes topically administering to the subject in need thereof a foamable composition manufactured as described herein, thereby treating the skin disorder or disease.

Particular corticosteroid-responsive conditions, such as corticosteroid-responsive dermatoses, that are treated using methods and topical foamable compositions of the present invention include but are not limited to inflammatory diseases such as allergic contact dermatitis, eczema, asteatotic eczema, discoid eczema, infantile eczema and diaper dermatitis, psoriasis; including plaque psoriasis, palmoplantar psoriasis, etc., seborrheic dermatitis, atopic dermatitis, dermatitis herpetiformis, neurodermatitis, lichen simplex chronicus, lichen planus, subacute cutaneous lupus erythematosus, urticaria, discoid lupus erythematosus, chronic hypertrophic lichen planus, granuloma annulare, keloid scars, reactions to insect and spider bites, *Pityriasis rosea*, erythema, and pruritus.

Methods and compositions of the present invention can be used for prophylaxis as well as amelioration of signs and/or symptoms of corticosteroid-responsive dermatoses. The terms "treating" and "treatment" used to refer to treatment of a corticosteroid-responsive dermatosis in a patient include preventing, inhibiting or ameliorating the corticosteroid-responsive dermatosis in the patient, such as slowing progression of the corticosteroid-responsive dermatosis and/or reducing or ameliorating a sign or symptom of the corticosteroid-responsive dermatosis.

A therapeutically effective amount of a topical foam composition of the present invention is an amount which has a beneficial effect on a corticosteroid-responsive dermatosis in a patient being treated. For example, a therapeutically effective amount of a composition of the present invention is effective to detectably decrease inflammation, crusting, scaling, erythema, induration, skin thickening and/or itching in a patient being treated for corticosteroid-responsive dermatosis.

Patients are identified as having, or at risk of having, a corticosteroid-responsive dermatosis using well-known medical diagnostic techniques.

The term "patient" or "subject" refers to an individual in need of treatment for a corticosteroid-responsive dermatosis. Human patients are particularly referred to herein although the terms are not limited to humans and encompass mammals as well as other animals, such as, but not limited to, non-human primates, cats, dogs, cows, horses, rodents, pigs, sheep, goats and poultry, and other animals in need of treatment for a corticosteroid-responsive dermatosis seen in veterinary practice.

The composition of the present invention may be administered acutely or over a period of weeks. For example, a composition as described herein may be topically administered at least once or twice, a day. Administration may include multiple doses administered topically over a period of days or weeks, such as for treatment of corticosteroid-responsive dermatosis or as multiple short courses of therapy over a period of months or years to prevent recurrence or flares of the inflammatory disease.

A therapeutically effective amount of a composition according to the present invention will vary depending on the particular formulation used, the severity of the corticosteroid-responsive dermatosis to be treated, the species of the patient, the age and sex of the subject and the general physical characteristics of the patient to be treated. One of skill in the art could determine a therapeutically effective amount in view of these and other considerations typical in medical practice. In general it is contemplated that a therapeutically effective amount, applied topically, would be determined by the area of body surface involved in the disease or condition and would likely be in the range of 0.5 gm-3.5 gm per application if administered twice a day. Further, dosage may be adjusted depending on whether treatment is to be acute or continuing.

Methods of treatment according to the present invention optionally include preparation of the area to be treated by cleansing with a suitable surfactant containing composition. The product can also be used in conjunction with a skin moisturizer.

The following examples are provided to further illustrate the embodiments of the present invention, but are not intended to limit the scope of the invention. While they are typical of those that might be used, other procedures, methodologies, or techniques known to those skilled in the art may alternatively be used.

EXAMPLE 1

Foamable Halobetasol Propionate Composition

A composition was prepared in accord with the present invention utilizing the formulation of Table VI above. Listed in Table VI is a specific composition based upon the ranges set forth hereinabove in Table I.

In this procedure as described in detail herein, a carrier solution is prepared by mixing and heating ethyl alcohol to between about 65°-70° C., adding benzoic acid, propylene glycol, Polyoxyl 20 cetostearyl ether, cetostearyl alcohol, and emulsifying wax and mixing to uniformity while maintaining a temperature of between about 65°-70° C. Water is added in multiple aliquots to maintain a temperature greater than 55° C. and the completed carrier solution is heated to 65°-70° C. The carrier solution is prepared in a vessel with a pressure and/or vacuum rated lid that seals onto the vessel in order to minimize evaporative losses during compounding. Then the carrier is cooled to about 45°-50° C. and the halobetasol propionate is added and mixed to uniformity. The solution is then filled into canisters while maintaining a temperature of between about 42°-48° C. and subsequently charged with propellant.

EXAMPLE 2

Skin Hydration and Transepidermal Water Loss (TEWL)

A series of studies was carried out to evaluate the properties and advantages of the composition of the present invention. These studies were carried out utilizing a preparation having a formulation in accord with Table VI as prepared by the procedure set forth above. In a first study, skin hydration was determined by use of an IBS Skicon-200 Conductance Meter equipped with a Measurement Technologies probe [unit 2283, probe A] to further enhance its ability to measure changes in skin surface hydration.

The data confirm that the composition of the present invention did not increase skin hydration when applied to shaved skin and was not considered to be occlusive. In fact, the composition decreased skin hydration (i.e., dehydrated) when applied to shaved skin.

A further study was carried out measuring transepidermal water loss (TEWL) of skin treated with the composition of the present invention. Computerized evaporimetry was measured with a recently calibrated cyberDERM RG1 Evaporimeter System (Broomall, Pa.) with TEWL Probes [unit RG1-09-048, probes 715 & 716] that were manufactured by Cortex Technology (Hadsund, Denmark).

The data confirm that the composition of the present invention when applied to shaved skin did not decrease TEWL.

Increased hydration of the skin is typically associated with an increased penetration of the active pharmaceutical ingredient (i.e., halobetasol) and consequently and increased efficacy. Similarly, a decrease in TEWL is associated with increased hydration, an increased penetration of the active pharmaceutical ingredient (i.e., halobetasol) and consequently an increased efficacy.

Unexpectedly, the composition tested does not appear to be acting as an occlusive since TEWL was not decreased and there was no increase in skin hydration.

EXAMPLE 3

Clinical Efficacy

A further experimental study evaluated the clinical efficacy of the composition of the present invention having the formulation of Table VI, described above, in the treatment of subjects with plaque psoriasis.

Results

52% of psoriasis subjects treated with the composition of the present invention having the formulation described above, and 0.0% of subjects treated with an identical composition void of halobetasol (Control Vehicle), achieved "treatment success".

Definitions:

Overall Disease Severity (ODS): At every visit, the overall severity of a subject's psoriasis in the Treatment Area, taking into consideration the three individual clinical signs of psoriasis (scaling, erythema, and plaque elevation) was assessed using a five-point scale ranging from 0=clear to 4=severe/very severe. To be enrolled in the study the subjects had to have at least a moderate ODS score (≥3).

| Clear (0) | |
|---|---|
| Scaling | No evidence of scaling. |
| Erythema | No erythema (hyperpigmentation may be present). |
| Plaque elevation | No evidence of plaque elevation above normal skin level. |
| Almost Clear (1) | |
| Scaling | Limited amount of very fine scales partially covers some of the plaques. |
| Erythema | Faint red coloration. |
| Plaque elevation | Very slight elevation above nonual skin level, easier felt than seen. |
| Mild (2) | |
| Scaling | Mainly fine scales; some plaques are partially covered. |
| Erythema | Light red coloration. |
| Plaque elevation | Slight but definite elevation above normal skin level, typically with edges that are indistinct or sloped, on some of the plaques. |
| Moderate (3) | |
| Scaling | Somewhat coarser scales predominate; most plaques are partially covered. |
| Erythema | Moderate red coloration. |
| Plaque elevation | Moderate elevation with rounded or sloped edges on most of the plaques. |
| Severe/Very Severe (4) | |
| Scaling | Coarse, thick tenacious scales predominate; virtually all or all plaques are covered; rough surface. |
| Erythema | Dusky to deep red coloration. |
| Plaque elevation | Marked to very marked elevation, with hard to very hard sharp edges on virtually all or all of the plaques. |

Clinical Signs of Plaque Psoriasis: At every visit, the average severity of each of the three key characteristics of plaque psoriasis (scaling, erythema and plaque elevation) in the Treatment Area was assessed using a five-point scale ranging from 0=clear to 4=severe/very severe.

| Scaling: | | |
|---|---|---|
| 0 | Clear | No evidence of scaling. |
| 1 | Almost clear | Limited amount of very fine scales partially covers some of the plaques. |
| 2 | Mild | Mainly fine scales predominate; some plaques are partially covered. |
| 3 | Moderate | Somewhat coarser scales predominate; most plaques are partially covered. |
| 4 | Severe/Very severe | Coarse, thick tenacious scales predominate; virtually all or all plaques are covered; rough surface. |
| Erythema: | | |
| 0 | Clear | No erythema (hyperpigmentation may be present). |
| 1 | Almost clear | Faint red coloration. |
| 2 | Mild | Light red coloration. |
| 3 | Moderate | Moderate red coloration. |
| 4 | Severe/Very severe | Dusky to deep red coloration. |
| Plaque Elevation: | | |
| 0 | Clear | No evidence of plaque elevation above normal skin level. |
| 1 | Almost clear | Very slight elevation above normal skin level, easier felt than seen. |
| 2 | Mild | Slight but definite elevation above normal skin level, typically with edges that are indistinct or sloped, on some of the plaques. |
| 3 | Moderate | Moderate elevation with rounded or sloped edges on most of the plaques. |
| 4 | Severe/Very severe | Marked to very marked elevation, with hard to very hard sharp edges on virtually all or all of the plaques. |

Pruritus: At every visit, the severity of pruritus was scored on a six-point scale from 0=none to 5=severe according to the following scale.

| Pruritus | | |
|---|---|---|
| 0 | None | No evidence of itching. |
| 1 | Mild | Only aware of itching at times, only present when relaxing, not present when focused on other activities. |
| 2 | Mild to Moderate | Intermediate between 1 and 3. |
| 3 | Moderate | Often aware of itching, annoying, sometimes disturbs sleep and daytime activities. |
| 4 | Moderate to Severe | Intermediate between 3 and 5. |
| 5 | Severe | Constant itching, distressing; frequent sleep disturbance, interferes with activities. |

To be enrolled into the study, subjects had to have at least moderate ODS score (at least 3). All ITT subjects satisfied that requirement with at least 85% of each treatment group (HBP: 87% or 20/23; VEH: 85% or 17/20) having moderate ODS, with the remainder of subjects having severe/very severe ODS In this study "treatment success" is indicated by a score of 0 or 1 for overall disease severity (ODS) and the clinical signs and symptoms of psoriasis. Further, the term "improved" refers to at least a two (2) grade decrease in severity score relative to Baseline for overall disease severity (ODS) and the clinical signs and symptoms of psoriasis. Note: Dichotomization of scores for clinical signs and symptoms of psoriasis will exclude subjects with Baseline scores of 0 or 1 unless the corresponding sign score at Day 8 or Day 15 is >1.

Figure 1:
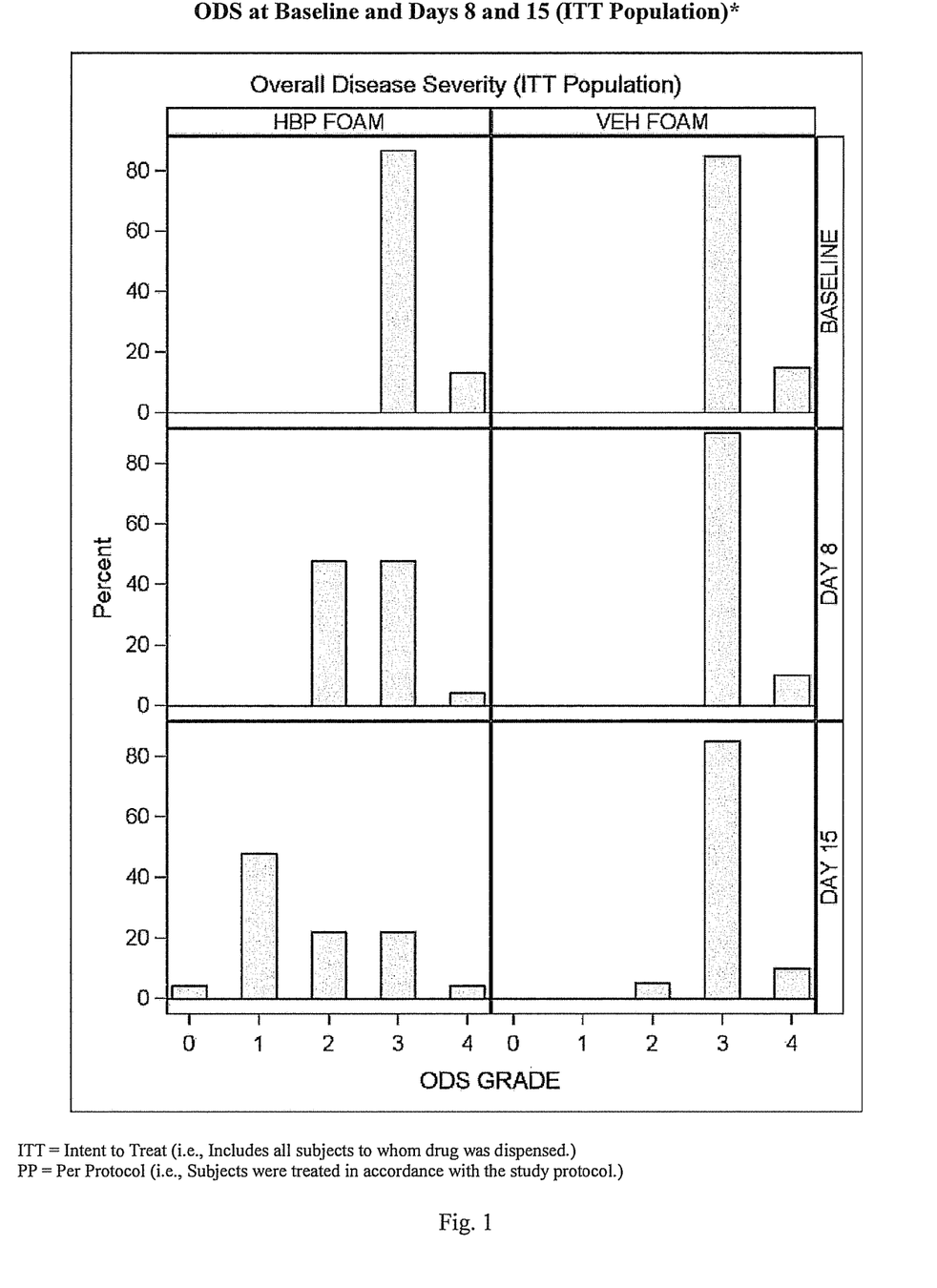
FIG. 1 is a graphical representation presenting clinical data relating to administration of compositions of the present invention in one embodiment of the invention.
Figure 2:
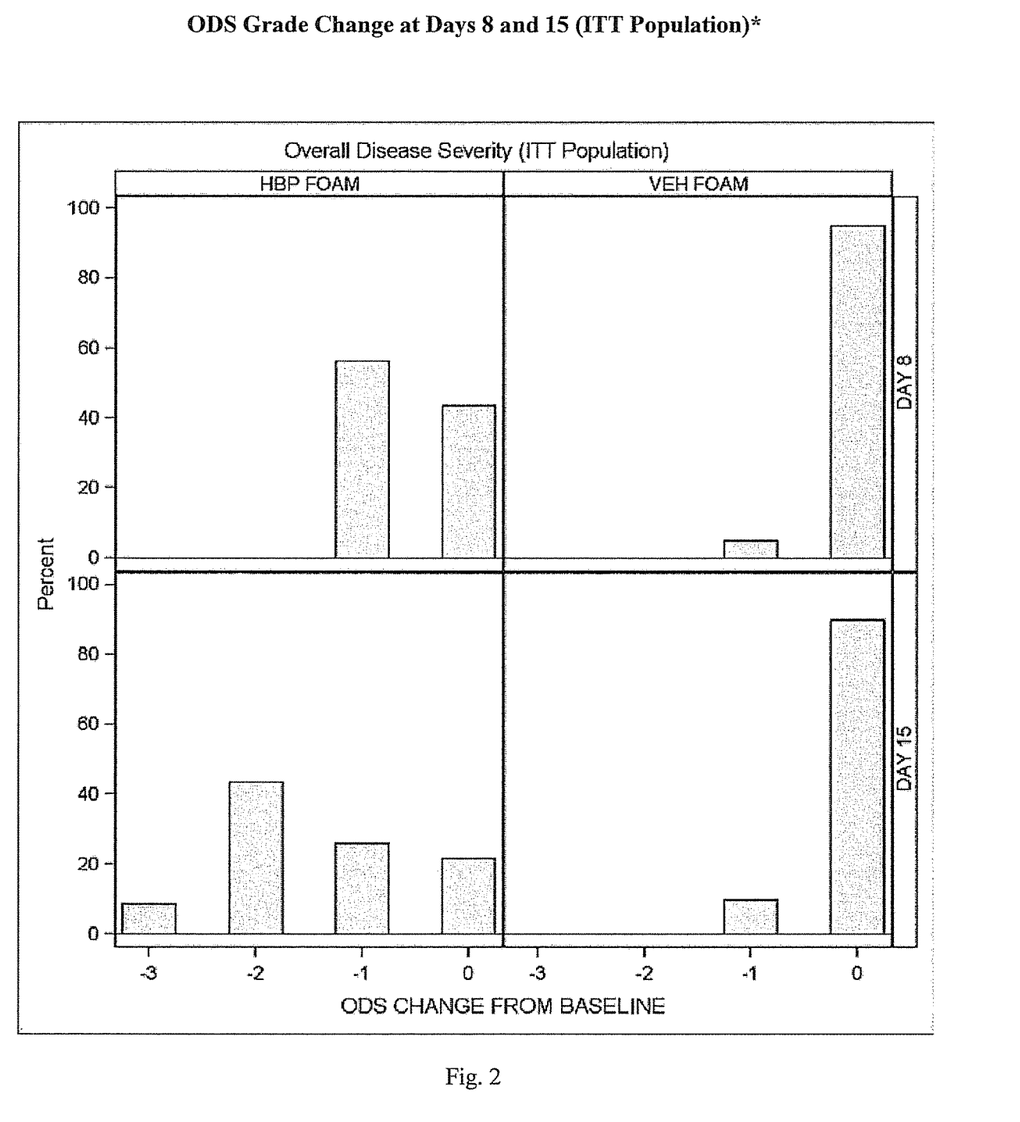
FIG. 2 is a graphical representation presenting clinical data relating to administration of compositions of the present invention in one embodiment of the invention.

As illustrated in FIG. 1, the ODS score remained unchanged (change=0) at Day 15 for the majority of vehicle group subjects (18/20; 90%) with the remaining subjects experiencing, at most, a one grade improvement. Only 21.7% (5/23) of the HBP subjects had no change in ODS score at Day 15 with the remaining subjects having a one to three grade decrease in score.

It was anticipated that a halobetasol cream would be more efficacious than halobetasol foam because creams are determined to be more occlusive. However, efficacy results for the composition set forth in Table VI were materially better than those obtained in the studies that supported Ultravate® Cream (halobetasol propionate) approval by the FDA.

In fact, "treatment success" results for the composition set forth in Table VI, were determined to be equal to or better than those published for all other forms of Class 1 topical steroid products containing halobetasol, fluocinonide and even what is believed to be the most potent steroid: clobetasol propionate. (See Table VII).

TABLE VII

Treatment Success
FDA Approved Class 1 Topical Corticosteroid Products (Study Drugs1-9) and
the Composition set forth in Table II herein (Study Drugs 10 and 11)
Treatment Success (or Improved) at 2 Weeks**

|   | Study Drug | Results | Control Drug | Results | Year Approved |
|---|---|---|---|---|---|
| 1 | Ultravate ® Cream (halobetasol propionate) (Study 1) | 3/38 (7.9%) | Vehicle | 0/39 (0.0%) | 1991 |
| 2 | Ultravate ® Cream (halobetasol propionate) (Study 2) | 7/40 (17.5%) | Vehicle | 0/40 (0.0%) | 1991 |
| 3 | Temovate ® E (clobetasol propionate) ITT | 12/51 (22%) | Vehicle | 1/46 (2%) (Includes Cleared and Excellent) | 1994 |
| 4 | Clobetasol propionate Lotion ITT 4 week study | 30/82 (36.6%) | Temovate E (clobetasol propionate) | 33/81 (40.7%) | 2003 |
| 5 | Clobetasol propionate Lotion PP 4 week study | 27/76 (35.5%) | Temovate E (clobetasol propionate) | 32/75 (42.7%) | 2003 |
| 6 | Vanos ® (fluocinonide) QD ITT | 19/107 (18%) | Vanos (fluocinonide) BID | 33/107 (31%) | 2005 |
| 7 | Vanos ® (fluocinonide) QD PP | 18/90 (20%) | Vanos (fluocinonide) BID | 31/97 (32%) | 2005 |
| 8 | Olux ® E Foam (clobetasol propionate) ITT | 41/253 (16%) | Temovate Ointment (clobetasol propionate) | 38/121 (31%) | 2007 |
| 9 | Olux ® E (clobetasol propionate) PP | 39/234 (17%) | Temovate Ointment (clobetasol propionate) | 34/111 (31%) | 2007 |
| 10 | Present Invention (halobetasol propionate) ITT | 12/23 (52.2%) | Vehicle | 0/20 (0.0%) | Currently In Development |
| 11 | Present Invention (halobetasol propionate) PP | 12/22 (54.5%) | Vehicle | 0/20 (0.0%) | Currently In Development |

**Note:
Studies 4 and 5 show results collected after 4 weeks of treatment. All the rest show results after only 2 weeks of treatment.
BID = Twice per day;
ITT = Intent to Treat Population;
PP = Per Protocol Population;
QD = Once per day It should be noted that over the years the FDA has changed the parameters defining clinical "success" and has progressively elevated the efficacy standard for "treatment success". The results obtained with the present halobetasol propionate foam composition were unexpectedly strong. The Ultravate® Cream results as shown in the first two rows of the Treatment Success Table VII were filed with the FDA as a basis of the NDA approval. It should also be noted that the results achieved with the halobetasol propionate foam composition of the present invention are superior to those achieved through the use of the Ultravate® Cream and are as good as or better than any of the other Class 1 topical corticosteroids.

Clobetasol propionate is generally believed to be a more potent steroid molecule than halobetasol propionate. As shown in Table VII, the results of a clinical trial that served as the basis of the FDA approval of Olux® E Foam reported 16% of the Olux® E Foam treated subjects and 31% of the Control subjects receiving Temovate® Ointment (0.05% clobetasol propionate) achieved "treatment success". Unexpectedly, inclusion of halobetasol propionate (as opposed to clobetasol propionate) in a foam formulation comparable to Olux® E Foam (which is not produced as described herein) produced a "treatment success" in 52.2% of those patients treated as compared to 16% of those who had been treated with Olux® E Foam.

The "treatment success" rate of 52% for the composition set forth in Table VI is unexpected because the similar Olux® E Foam formulation containing the more potent molecule (i.e., clobetasol propionate) only achieved a 16% rate. These results are indeed unexpected given the relative potencies of halobetasol propionate and clobetasol propionate. One would expect a comparable composition including halobetasol (i.e., the formulation of Table VI), which is considered less potent than clobetasol, to be less efficacious than Olux® E Foam. These results show unexpected beneficial therapeutic effects were achieved through use of the composition of the present invention.

EXAMPLE 4

Formulation Stability

A composition was prepared in accord with the present invention utilizing the formulation of Table VI above. The composition was filled into canisters that were charged with propellant. The contents of the canister were analyzed by high-performance liquid chromatography (HPLC) for halobetasol propionate content and associated degradation products. The pH of the canister contents was also measured. Additional canisters were placed on stability at 25°±2° C.

and 60%±5% relative humidity, the ICH long-term storage condition. Fresh samples were analyzed after 1-, 3-, 6-, 9-, 12-, and 18-months of storage.

Figure 3:
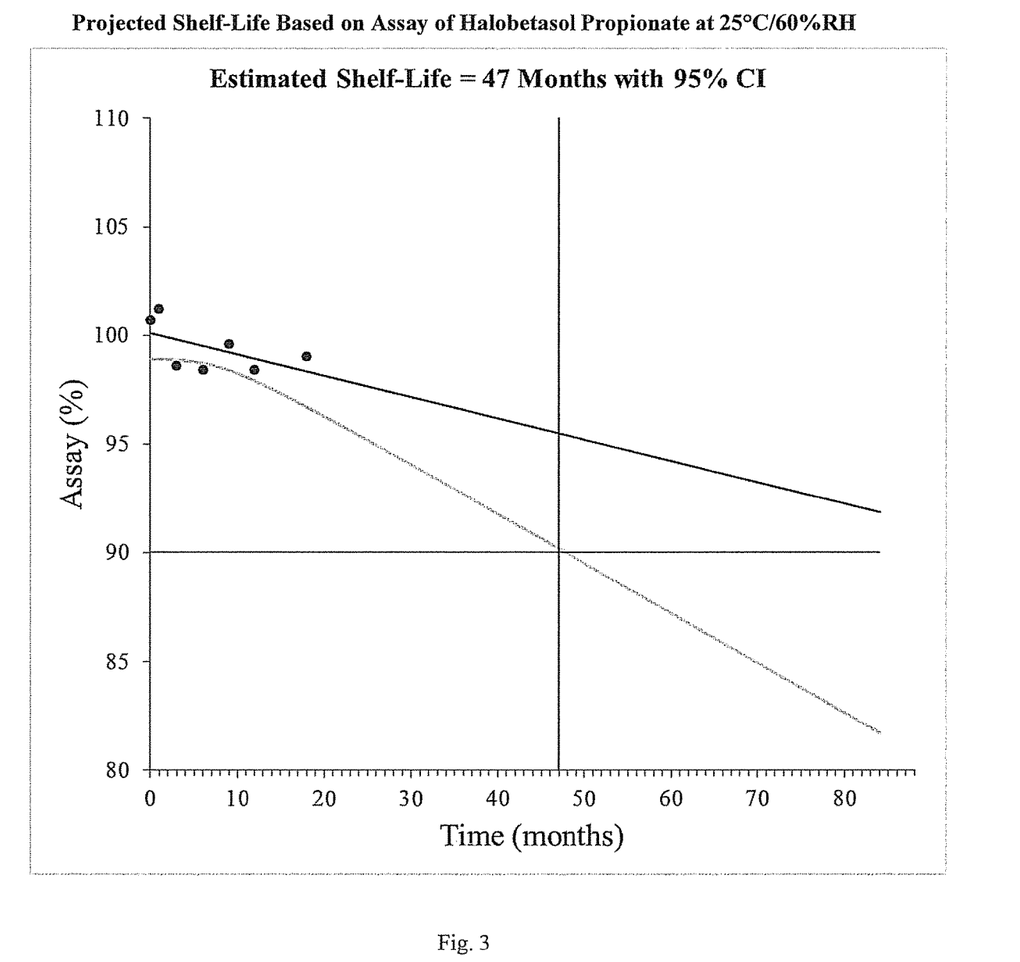
FIG. 3 is a graphical representation presenting stability data relating to the projected shelf-life of the compositions of the present invention in one embodiment of the invention, based on assaying the active ingredient.

The assay results were plotted against the storage duration in months. The linear regression was determined for the assay data. The 95% one-side lower confidence interval was determined for the linear regression. The resulting predicted shelf-life was unexpectedly greater than 36 months as shown in FIG. 3.

Figure 4:
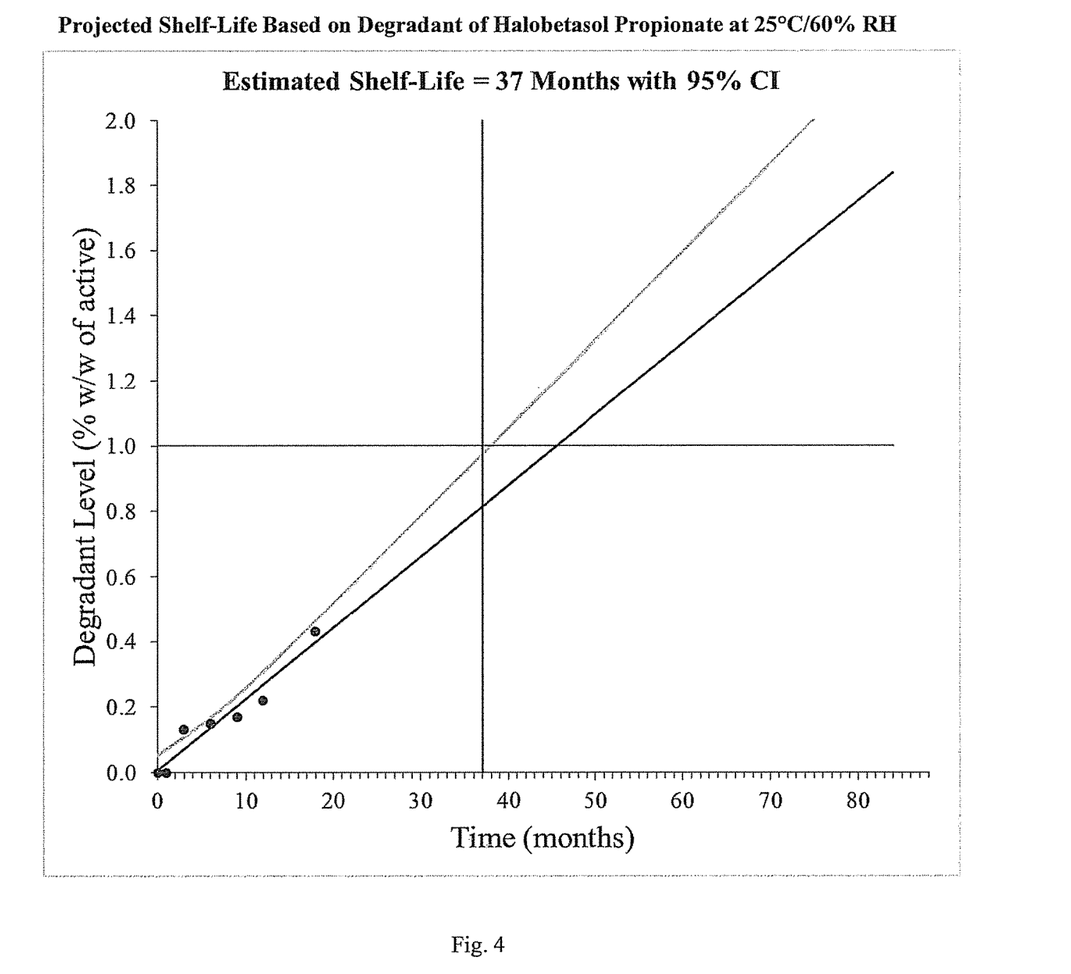
FIG. 4 is a graphical representation presenting stability data relating to the projected shelf-life of the compositions of the present invention in one embodiment of the invention, based on assaying a degradation product of the active ingredient.

The degradant results were plotted against the storage duration in months. The linear regression was determined for the degradant data. The 95% one-side upper confidence interval was determined for the linear regression. The resulting predicted shelf-life was unexpectedly greater than 36 months as shown in FIG. 4.

Figure 5:
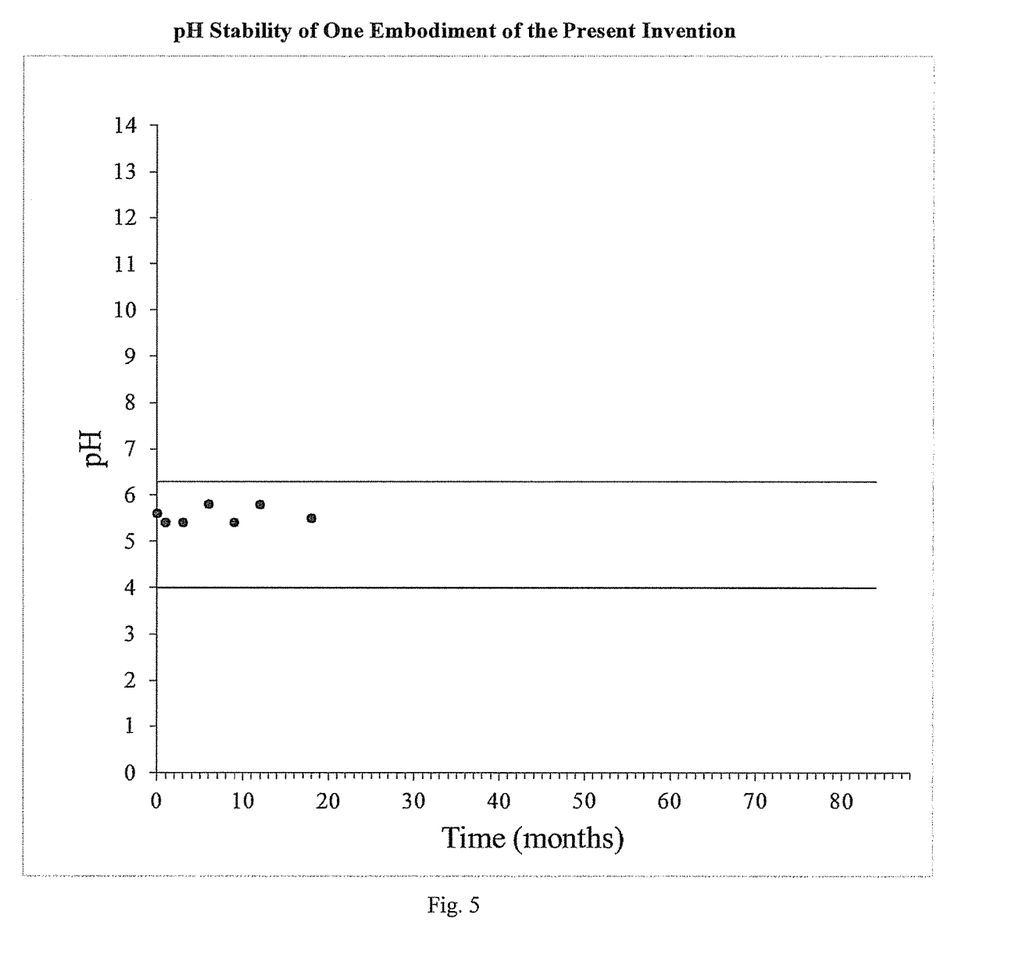
FIG. 5 is a graphical representation presenting stability data relating to the pH of the compositions of the present invention in one embodiment of the invention.

Unexpectedly, no significant change and no trending were observed with the pH data for the unbuffered formulation. Therefore, no formal statistical analysis was performed on the pH data in order to project the shelf-life. The pH data are shown in FIG. 5.

Although the invention has been described with reference to the above example, it will be understood that modifications and variations are encompassed within the spirit and scope of the invention. Accordingly, the invention is limited only by the following claims.

What is claimed is:

1. A method for treating a skin disease, condition or disorder in a subject, the method comprising topically administering to the subject a composition, the composition comprising, on a weight basis:
   a) 0.02 to 0.10% halobetasol or its pharmaceutically acceptable salts, esters, and solvates;
   b) 40 to 60% ethyl alcohol;
   c) 0.1 to 5.0% Emulsifying Wax, NF;
   d) 0.05 to 1.0% cetostearyl alcohol;
   e) 0.05 to 1.0% polyoxyl 20 cetostearyl ether;
   f) 1 to 10% propylene glycol;
   g) 30 to 40% water;
   h) greater than 0.0% and less than 0.0005% benzoic acid; and
   i) 3.25 to 5.75% propellant, wherein the composition has a pH of between about 4.0 to 6.3,
wherein the composition is void of a buffer system.

2. The method of claim 1, wherein the skin disease, condition or disorder is selected from the group consisting of allergic contact dermatitis, eczema, asteatotic eczema, discoid eczema, infantile eczema, diaper dermatitis, psoriasis; plaque psoriasis, palmoplantar psoriasis, seborrheic dermatitis, atopic dermatitis, dermatitis herpetiformis, neurodermatitis, lichen simplex chronicus, lichen planus, subacute cutaneous lupus erythematosus, urticaria, discoid lupus erythematosus, chronic hypertrophic lichen planus, granuloma annulare, keloid scars, reactions to insect and spider bites, *Pityriasis rosea*, erythema, and pruritis.

3. The method of claim 1, wherein the subject is a human.

4. The method of claim 1, wherein the composition is administered once daily, twice daily, weekly, biweekly, or monthly.

5. The method of claim 1, wherein the administration does not decrease transepidermal water loss (TEWL) at the treated administration site.

6. The method of claim 1, wherein the administration does not increase skin hydration at the treated administration site.

7. The method of claim 1, wherein the administration does not decrease transepidermal water loss (TEWL) at the treated administration site and does not increase skin hydration at the treated administration site.

8. The method of claim 1, wherein the skin disease, condition or disorder is psoriasis.

9. The method of claim 2, wherein the skin disease, condition or disorder is plaque psoriasis.

10. The method of claim 4, wherein the composition is administered once daily.

11. The method of claim 4, wherein the composition is administered twice daily.

* * * * *